(12) United States Patent
Park et al.

(10) Patent No.: US 10,080,546 B2
(45) Date of Patent: Sep. 25, 2018

(54) THREE-DIMENSIONAL ULTRASONIC PROBE

(71) Applicant: SAMSUNG MEDISON CO., LTD., Hangcheon-gun, Gangwon-do (KR)

(72) Inventors: Jun-woo Park, Gangwon-do (KR); Gil-ju Jin, Gangwon-do (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 258 days.

(21) Appl. No.: 14/661,845

(22) Filed: Mar. 18, 2015

(65) Prior Publication Data

US 2015/0265244 A1    Sep. 24, 2015

(30) Foreign Application Priority Data

Mar. 19, 2014  (KR) .................. 10-2014-0032166

(51) Int. Cl.
  *A61B 8/12* (2006.01)
  *A61B 8/00* (2006.01)
  *A61B 8/08* (2006.01)
  *G01S 15/89* (2006.01)

(52) U.S. Cl.
  CPC .......... *A61B 8/4461* (2013.01); *A61B 8/0866* (2013.01); *A61B 8/12* (2013.01); *A61B 8/4488* (2013.01); *A61B 8/483* (2013.01); *G01S 15/894* (2013.01); *G01S 15/8915* (2013.01); *G01S 15/8993* (2013.01)

(58) Field of Classification Search
  None
  See application file for complete search history.

(56) References Cited

U.S. PATENT DOCUMENTS

| 5,152,294 A | 10/1992 | Mochizuki et al. |
| 5,313,950 A | 5/1994 | Ishikawa et al. |
| 5,740,804 A * | 4/1998 | Cerofolini ................ A61B 8/12 600/459 |
| 6,423,008 B1 | 7/2002 | Okawa et al. |
| 2005/0124889 A1* | 6/2005 | Flesch .................. A61B 8/4281 600/445 |
| 2006/0241453 A1* | 10/2006 | Nguyen-Dinh .......... A61B 8/00 600/445 |
| 2007/0016060 A1 | 1/2007 | Hwang |
| 2008/0161695 A1 | 7/2008 | Kim et al. |
| 2009/0306516 A1 | 12/2009 | Oonuki et al. |

(Continued)

FOREIGN PATENT DOCUMENTS

| CN | 102599934 A * | 7/2012 |
| EP | 0514584 A2 | 11/1992 |

(Continued)

OTHER PUBLICATIONS

Extended European Search Report issued in corresponding European Application No. 14195430.5-1812, dated Aug. 13, 2015.

*Primary Examiner* — Amanda Lauritzen Moher
*Assistant Examiner* — Farouk Bruce
(74) *Attorney, Agent, or Firm* — McDermott Will & Emery LLP

(57) ABSTRACT

Provided is a three-dimensional (3D) ultrasonic probe that may diagnose all regions of an object to be diagnosed without being limited by a rotation angle by allowing a rotation axis of a driving unit to be directly connected to an ultrasonic transducer.

5 Claims, 7 Drawing Sheets

(56) References Cited

U.S. PATENT DOCUMENTS

2011/0071398 A1    3/2011  Hwang et al.
2011/0224551 A1*  9/2011  Barnard .................. A61B 8/08
                                                        600/445

FOREIGN PATENT DOCUMENTS

| EP | 2601893 A1 | 6/2013 |
| --- | --- | --- |
| KR | 10-2008-0063964 A | 7/2008 |
| KR | 10-2012-0088642 A | 8/2012 |

* cited by examiner

THREE-DIMENSIONAL ULTRASONIC PROBE

RELATED APPLICATION

This application claims the benefit of Korean Patent Application No. 10-2014-0032166, filed on Mar. 19, 2014, in the Korean Intellectual Property Office, the disclosure of which is incorporated herein in its entirety by reference.

BACKGROUND

1. Field

One or more embodiments of the present invention relate to a three-dimensional (3D) ultrasonic probe.

2. Description of the Related Art

Examples of representative medical ultrasonic devices may include a diagnostic ultrasound imaging device that is mainly used to contrast an organ or a fetus in a human body. A diagnostic ultrasound imaging device has advantages in that the diagnostic ultrasound imaging device may contrast a specific point in a human body desired to be seen by a doctor who makes a diagnosis by enabling the doctor to arbitrarily adjust a radiation angle of ultrasound, unlike other medical devices for contrasting internal body structures such as an X-ray device, a computed tomography (CT) device, or a magnetic resonance imaging (MRI) device, and the diagnostic ultrasound imaging device has no radiation risks and may obtain an image in a shorter time than that of the other medical devices.

In order to obtain an image, a diagnostic ultrasound imaging device needs an ultrasonic probe or an ultrasonic transducer that is a unit and/or a device for converting an ultrasound signal into an electrical signal or an electrical signal into an ultrasound signal. The ultrasonic probe generally includes an ultrasonic module that includes a piezoelectric layer that converts an electrical signal into a sound signal or a sound signal into an electrical signal when a piezoelectric material vibrates, a matching layer that reduces an acoustic impendence difference between the piezoelectric layer and a human body in order for ultrasound that is generated in the piezoelectric layer to be transmitted to a target point of the human body as much as possible, a lens layer that focuses the ultrasound that travels to the front of the piezoelectric layer on a specific point, and a sound-absorbing layer that prevents image distortion by preventing the ultrasound from traveling to the back of the piezoelectric layer. Although the ultrasonic probe may include a single ultrasonic transducer when being used for special purposes, the ultrasonic probe generally includes a plurality of ultrasonic transducers when being used for medical purposes.

Ultrasonic probes for medical purposes may be classified according to the number of ultrasonic transducers, an arrangement method of ultrasonic transducers, a shape of an array axis of ultrasonic transducers, or an application field. When classified according to the number of ultrasonic transducers, ultrasonic probes for medical purposes may be classified into single transducer type ultrasonic probes and multi-transducer type ultrasonic probes. In this case, multi-transducer type ultrasonic probes may be classified according to an array method of ultrasonic transducers into one-dimensional (1D) array ultrasonic probes in which ultrasonic transducers are arranged on a single axis and two-dimensional (2D) array ultrasonic probes in which ultrasonic transducers are arranged on a plurality of axes that intersect each other. 1D array ultrasonic transducers may be classified according to a shape of an array axis of ultrasonic transducers into linear array ultrasonic probes and curvilinear array ultrasonic probes.

1D array ultrasonic transducers that are the most often used may obtain only a 2D image at a point in front of an ultrasonic transducer because of the linearity of ultrasound. Accordingly, existing 1D array ultrasonic probes have problems in that it is difficult to make an accurate diagnosis and it is impossible to contrast a 3D shape of a fetus or a movement of a fetus as a moving image. Recently, there has been a demand for ultrasonic probes that may obtain a 3D image in a human body, in particular, a 3D dynamic image. A 3D image may be obtained by using an existing 1D array ultrasonic probe and or a 2D array ultrasonic probe.

A 2D array ultrasonic probe has problems in that since the 2D array ultrasonic probe includes an extremely larger number of ultrasonic transducers than a 1D array ultrasonic probe, a manufacturing process is complex, and since an image obtained by using the 2D array ultrasonic probe has a low signal-to-noise (S/N) ratio, the quality of the image is low. Accordingly, a method of obtaining a 3D image by using a 1D array ultrasonic probe has recently been continuously studied.

In order to obtain a 3D image by using a 1D array ultrasonic probe, a doctor who makes a diagnosis moves the 1D array ultrasonic probe manually or mechanically. A 1D array ultrasonic probe that obtains a 3D image by being manually manipulated by a doctor who makes a diagnosis has problems in that the quality of an image is very low due to an irregular contrast interval and an error of the 3D image increases according to doctors who make a diagnosis. Accordingly, recently, a method of obtaining a 3D image by mechanically moving a 1D array ultrasonic probe has been actively studied.

Examples of a method of obtaining a 3D image by mechanically moving a 1D array ultrasonic probe may include a method of moving an array axis of ultrasonic transducers in parallel and a method of rotating an array axis of ultrasonic transducers by a predetermined angle. The former method in which an array axis of ultrasonic transducers is moved by using a motor to be parallel to a region of a body to be contrasted has advantages in that a contrast interval of a 3D image is kept uniform and an erroneous occurrence of the 3D image is reduced, but has disadvantages in that since an overall size of an ultrasonic probe including a power generating unit such as the motor is considerably large, it is difficult to manufacture and use the ultrasonic probe.

In contrast, the latter method in which an array axis of ultrasonic transducers is rotated by a predetermined angle over a region of a body to be contrasted along an arc path by using a power generating unit such as a motor has advantages in that since an overall size of an ultrasonic probe is smaller than that of the former method, the usability of the ultrasonic probe is excellent.

Ultrasonic probes that obtain a 3D image by rotating an array axis of ultrasonic transducers may be classified into one-element ultrasonic probes in which a module including ultrasonic transducers and a power generating unit such as a motor are located in a single housing and two-element ultrasonic probes in which a module and a power generating unit are not located in a single housing but are separately located. Two-element ultrasonic probes in which a module and a power generating unit that are not located in the same housing are coupled to each other by a separate element have advantages in that a 2D cross-sectional image may be obtained by using an existing 1D array ultrasonic probe, but have disadvantages in that since the power generating unit is independently located from the module, an overall size of a two-element ultrasonic probe is considerably larger than that of a one-element ultrasonic probe and thus the usability of the two-element ultrasonic probe is low.

In contrast, one-element ultrasonic probes in which a module and a power generating unit are located in the same housing have advantages that since an overall size of a one-element ultrasonic probe is smaller than that of a two-element ultrasonic probe, the ultrasonic probe may be manufactured to have a small size.

However, existing one-element ultrasonic probes have low manufacturability and low durability since a mechanical driving relationship for rotating an array axis of ultrasonic transducers by a predetermined angle is complex. In addition, one-element ultrasonic probes have problems in that although an array axis of ultrasonic transducers has to be rotated by a rotation angle that is as wide as possible in order to obtain an image having better quality, since there is a limitation in the rotation angle due to a wire structure, utilization during diagnosis is reduced, and since an internal structure is complex and air bubbles are stuck at every corner, it is difficult to remove oil. Also, one-element ultrasonic probes have problems in that since a motor and a power transmitting unit that are disposed in a probe occupy a large space, it is difficult to miniaturize the probe, and since additional oil exists in a place where the motor and the power transmitting unit are disposed, it is difficult to lighten the probe. Also, one-element ultrasonic probes have problems in that noise and vibration may occur in a power transmitting unit for transmitting power from a motor.

SUMMARY

One or more embodiments of the present invention include a three-dimensional (3D) ultrasonic probe which may improve driving performance and reduce a weight, noise, a manufacturing time, and manufacturing costs by providing the 3D ultrasonic probe driving apparatus at both ends of an ultrasonic transducer and directly driving the ultrasonic transducer.

Additional aspects will be set forth in part in the description which follows and, in part, will be apparent from the description, or may be learned by practice of the presented embodiments.

According to one or more embodiments of the present invention, a three-dimensional (3D) ultrasonic probe includes: an ultrasonic transducer in which ultrasound transmitting/receiving elements are arranged; and a first driving unit that is disposed such that a rotation axis of the first driving unit is fixed to one end portion of the ultrasonic transducer, and directly transmits power to the ultrasonic transducer.

The 3D ultrasonic probe may further include a second driving unit that is disposed such that a rotation axis of the second driving unit is fixed to the other end portion of the ultrasonic transducer, and directly transmits power to the ultrasonic transducer.

The ultrasound transmitting/receiving elements may be aligned on a top surface of the ultrasonic transducer.

The first and the second driving unit may be a motor including a rotor that is disposed at a central portion of the motor and a plurality of stators that surround the central portion of the motor, wherein when the motor of the first and second driving unit is respectively disposed at either end portion of the ultrasonic transducer, the stators of the motor which are disposed at the both end portions to face each other are symmetric to each other.

The first and second driving unit may be a motor including a rotor that is disposed at a central portion of the motor and a plurality of stators that surround the central portion of the motor, wherein when the motor of the first and second driving unit is respectively disposed at either end portion of the ultrasonic transducer, the stators of the motor which are disposed at the both end portions to face each other are asymmetric to each other.

The motor may be a servo motor or a step motor.

A rotation angle of the ultrasonic transducer may be equal to or greater than 120° and equal to or less than 360°.

The 3D ultrasonic probe may be any one of an endocavity probe and a convex probe.

According to an embodiment of the present invention, since rotation axes of driving units are directly connected to both end portions of an ultrasonic transducer, a complex and sophisticated mechanical portion does not need to be added to a 3D ultrasonic probe. Accordingly, since an additional space for disposing a motor and a power transmitting unit in the 3D ultrasonic probe and oil that needs to exist in the additional space are not necessary, the 3D ultrasonic probe may be miniaturized and lightened. Also, since a manufacturing process is simplified, a manufacturing time and manufacturing costs may be reduced. In addition, since a connection driving unit such as a gear and a wire is omitted, noise may be removed, rotation backrush may be avoided, and a limitation in a driving speed and a driving angle due to the complex and sophisticated mechanical portion may be reduced. Also, since an internal structure is simplified, air bubbles may be easily removed, a failure rate may be reduced, and an angle of a module may be adjusted according to a method of using a step motor or a servo motor.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
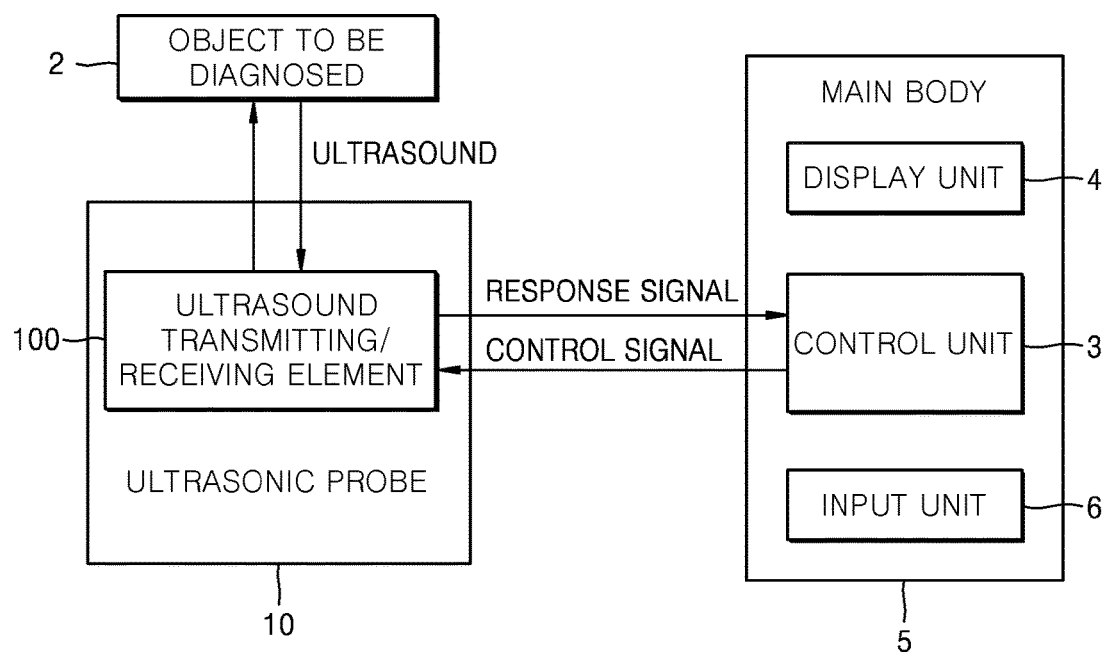
FIG. 1 is a block diagram illustrating essential elements of a three-dimensional (3D) ultrasonic probe.

The present invention will now be described more fully with reference to the accompanying drawings for those of ordinary skill in the art to be able to perform the present invention without any difficulty. The invention may, however, be embodied in many different forms and should not be construed as being limited to the embodiments set forth herein; rather, these embodiments are provided so that this disclosure will be thorough and complete, and will fully convey the concept of the invention to those of ordinary skill in the art. Also, parts in the drawings unrelated to the detailed description may be omitted to ensure clarity of the present invention, and widths, lengths, and thicknesses of elements in the drawings may be exaggerated for convenience. Like reference numerals in the drawings denote like elements, and thus their description will not be repeated.

It will be further understood that when a part "includes" or "comprises" an element, unless otherwise defined, the part may further include other elements, not excluding the other elements.

As used herein, the term "and/or" includes any and all combinations of one or more of the associated listed items. Expressions such as "at least one of," when preceding a list of elements, modify the entire list of elements and do not modify the individual elements of the list.

FIG. 1 is a block diagram illustrating essential elements of a three-dimensional (3D) ultrasonic probe 10.

Referring to FIG. 1, the 3D ultrasonic probe 10 transmits an ultrasound signal to an object 2 and receives an ultrasound echo signal reflected from the object 2 by using an ultrasound transmitting/receiving element 100 while moving along a surface of the object 2 in a state where a front surface of the 3D ultrasonic probe closely contacts the surface of the object 2.

A main body 5 includes an input unit 6, a control unit 3, and a display unit 4 in order to receive a response signal from the ultrasound transmitting/receiving element 100 and to transmit a control signal to the ultrasound transmitting/receiving element 10. The input unit 6 may receive a diagnosis command for using the 3D ultrasonic probe 10, for example, an on/off signal of the 3D ultrasonic probe 10, may be input to the input unit 6. A button and a knob (not shown) for inputting various operation commands may be provided in the input unit 6. The control unit 3 may obtain an image of internal tissue of the object 2 by detecting a characteristic value of the internal tissue of the object 2 by using the response signal that is received from the 3D ultrasonic probe 10. The display unit 4 that is a unit for visually displaying the image of the internal tissue obtained by the control unit 3 may include an image display device such as a liquid crystal display (LCD) device, a cathode-ray tube (CRT), or an electric bulletin board using a light-emitting display (LED).

Figure 2:
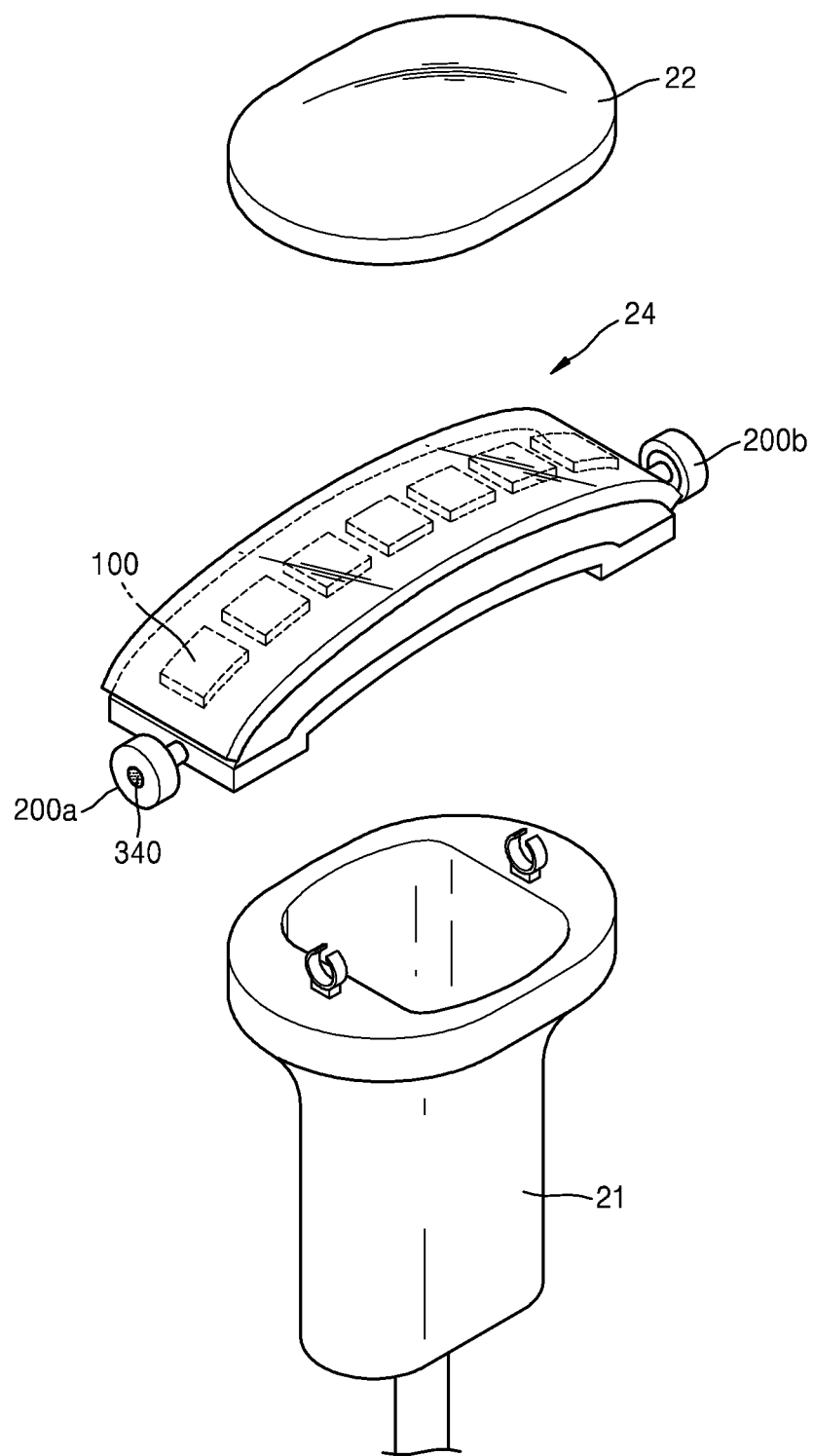
FIG. 2 is an enlarged perspective view illustrating the three-dimensional (3D) ultrasonic probe according to an embodiment of the present invention.
Figure 3:
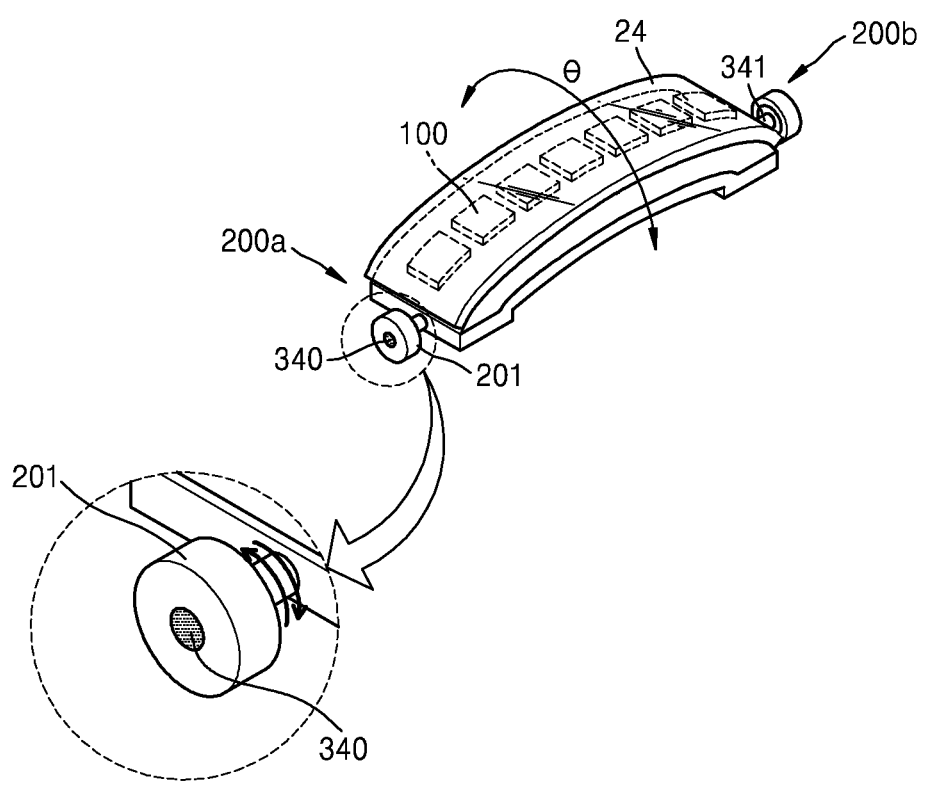
FIG. 3 is a perspective view illustrating an ultrasonic transducer of FIG. 2.

FIG. 2 is an enlarged perspective view illustrating the 3D ultrasonic probe 10 including a first driving unit 200a and a second driving unit 200b, according to an embodiment of the present invention. FIG. 3 is a perspective view illustrating an ultrasonic transducer 24 of FIG. 2.

Referring to FIG. 2, the 3D ultrasonic probe 10 includes a handle case 21, a cap 22 that is disposed at a front end of the handle case 21 and contacts the object 2 to be diagnosed, the ultrasonic transducer 24 that includes the first and second driving units 200a and 200b that generate a rotational force, and the ultrasonic transducer 24 that includes a plurality of the ultrasound transmitting/receiving elements 100 and rotates by receiving the rotational force from the first and second driving units 200a and 200b.

The cap 22 is formed such that a portion of the cap 22 corresponding to the ultrasonic transducers 24 has an arc-like cross-sectional shape in order to maintain a constant interval between an inner surface of the cap 22 and an outer surface of the ultrasonic transducer 24 even when the ultrasonic transducer 24 that is provided in the cap 22 rotates.

The ultrasound transmitting/receiving elements 100 that are each a unit for transmitting ultrasound into the object 2 and receiving a response signal reflected from each tissue in the object 2 convert a sound signal into an electrical signal by using the piezoelectric effect or magnetostriction effect, and transmit the electrical signal to a control unit (not shown). Examples of the ultrasound transmitting/receiving elements 100 may include piezoelectric micromachined ultrasonic transducers (pMUTs), capacitive micromachined ultrasonic transducers (cMUTs), and magnetic micromachined ultrasonic transducers (Mmuts).

The ultrasonic transducer 24 including the ultrasound transmitting/receiving elements 100 may be rotatably provided in the cap 22 as described above to read a 3D image of the object 2 to be diagnosed. The ultrasonic transducer 24 of FIG. 2 is a one-dimensional (1D) array ultrasonic transducer in which the ultrasound transmitting/receiving elements 100 are aligned. In order to obtain a 3D image by using the ultrasonic transducer 24 that is a 1D array ultrasonic transducer, the ultrasonic transducer 24 has to rotate within a predetermined angle range.

In a conventional ultrasonic probe, a separate driving unit for transmitting power to rotate the ultrasonic transducer 24 is provided. Power generated by the driving unit is transmitted to a rotation axis of the ultrasonic transducer 24 by disposing a wire between a pulley that is connected to a rotation axis of the driving unit and a pulley that is connected to the rotation axis of the ultrasonic transducer 24. The conventional ultrasonic probe has problems in that due to the pulleys and the wire, a rotation angle of the ultrasonic transducer 24 is limited to a predetermined range.

Referring to FIG. 3, in the 3D ultrasonic probe 10, the first and second driving units 200a and 200b are disposed at both end portions of the ultrasonic transducer 24 so that a 3D image may be obtained by pivoting by a predetermined angle the ultrasonic transducer 24 in which the ultrasound transmitting/receiving elements 100 are aligned.

In order to rotate the ultrasonic transducer 24, the first driving unit 200a or/and the second driving unit 200b may be disposed at one end portion or both end portions of the ultrasonic transducer 24. In this case, rotation axes 340 and 341 of the first and second driving units 200a and 200b may be fixed to the both end portions of the ultrasonic transducers in order for the ultrasonic transducer 24 to be directly driven by the first and second driving units 200a and 200b. For example, in FIG. 3, a main body 210 of any of the first and second driving units 200a and 200b for rotating the ultrasonic transducer 24 may be formed to have an annular shape, and the rotation axes 340 and 341 of the first and second driving units 200a and 200b may be fixed to the both end portions of the ultrasonic transducer 24 to transmit power and to function as hinge units. Accordingly, a rotational force for rotating the ultrasonic transducer 24 may be directly transmitted from the first and second driving units 200a and 200b without additionally providing a connection member such as a wire or a pulley, and thus an overall structure may be miniaturized and lightened. Also, since a manufacturing process is simplified, a manufacturing time and manufacturing costs may be reduced. In addition, since the first and second driving units 200a and 200b are disposed at the both end portions of the ultrasonic transducer 24, an inner space of the ultrasonic transducer 24 may be additionally secured. Accordingly, since a connection circuit that is connected to the plurality of ultrasound transmitting/receiving elements 100 may be easily constructed, and thus an analog driving unit such as a wire and a pulley is omitted, noise and rotation backrush may be removed, and since an internal structure is simplified, air bubbles may be easily removed and thus a failure rate may be reduced.

In FIGS. 2 and 3, a step motor or a servo motor including a rotor that rotates about a stator may be used as each of the first and second driving units 200a and 200b. A rotational force that is generated by the first and second driving units 200a and 200b may be directly transmitted to the ultrasonic transducer 24 by disposing the rotation axes 340 and 341 of the first and second driving units 200a and 200b at the both end portions of the ultrasonic transducer 24. However, the present embodiment is not limited to the step motor or the servo motor, and any other type of unit may be used as each of the first and second driving units 200a and 200b as long as the unit may directly transmit a rotational force that is generated by the first and second driving units 200a and 200b to the ultrasonic transducer 24.

In FIGS. 2 and 3, although the first driving unit 200a may be formed at one end portion of the ultrasonic transducer 24, when a sufficient rotational force has to be guaranteed or rotation of the ultrasonic transducer 24 has to be precisely adjusted, the first and second driving units 200a and 200b may be disposed at the both end portions of the ultrasonic transducer 24.

Figure 4A:
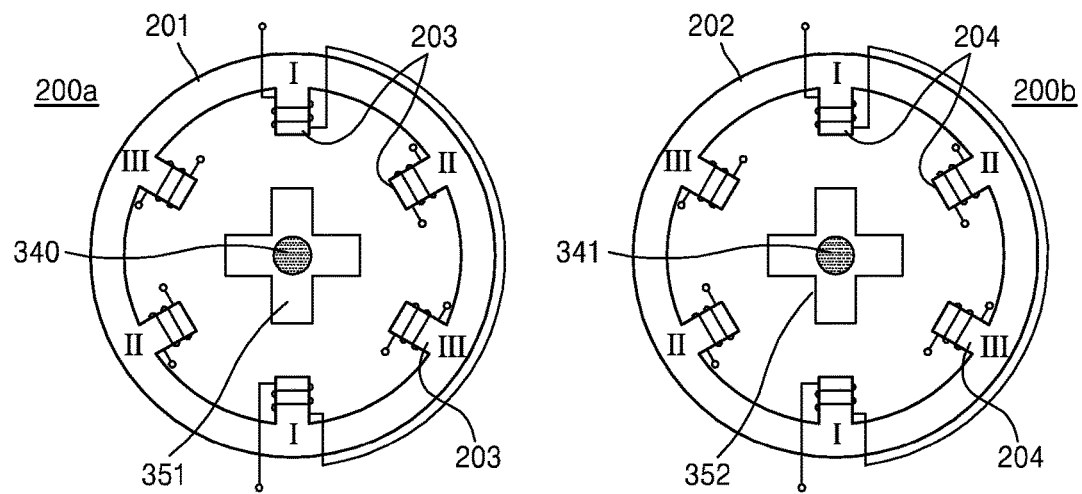
FIGS. 4A and 4B are cross-sectional views illustrating first and second step motors, according to embodiments of the present invention.
Figure 4B:
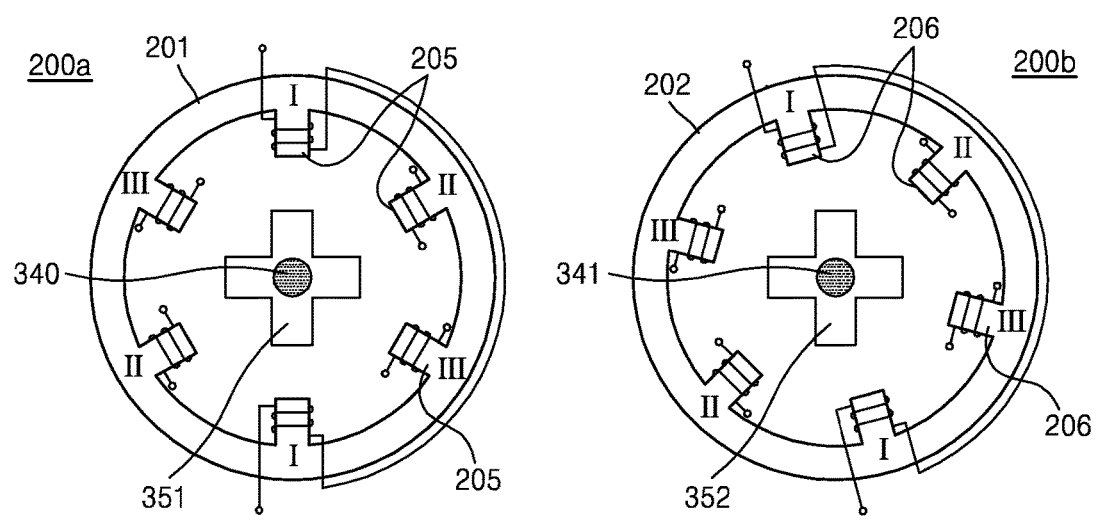

FIGS. 4A and 4B are cross-sectional views illustrating first and second step motors 201 and 202 that are used as the first and second driving units 200a and 200b, according to embodiments of the present invention.

Referring to FIGS. 4A and 4B, the first and second step motors 201 and 202 that are used as the first and second driving units 200a and 200b may include rotors 351 and 352 respectively including the rotation axes 340 and 341 and stators 203, 204, 205, and 206 that each surround the rotors 351 and 352. The stators 203, 204, 205, and 206 are disposed to be symmetric to each other about the rotors 351 and 352. Driving steps of the first and second step motors 201 and 202 are determined by an arrangement of the stators 203, 204, 205, and 206. When a greater driving force has to be guaranteed or more precise control is necessary, an arrangement of the first and second step motors 201 and 202 may be changed.

Referring to FIG. 4A, the first and second step motors 201 and 202 are disposed at both end portions of the ultrasonic transducer 24 such that the stators 203 and 204 at the both end portions of the ultrasonic transducer 24 are symmetric to each other. Since the stators 203 and 204 of the first and second step motors 201 and 202 that are disposed at the both end portions of the ultrasonic transducer 24 are disposed to be symmetric to each other, driving forces of the first step motor 201 and the second step motor 202 may be simultaneously applied to the ultrasonic transducer 24, and thus a greater driving force at each step may be guaranteed. When each step of each of the first and second step motors 201 and 202 is sub-divided, the first and second step motors 201 and 202 may be more precisely controlled. To this end, steps corresponding to the first step motor 201 and the second step motor 202 that are disposed at the both end portions of the ultrasonic transducer 24 have to occur at different times.

Referring to FIG. 4B, since the stators 206 of the second step motor 202 are disposed not to be symmetric to the stators 205 of the first step motor 201, driving steps of the first step motor 201 and the second step motor 202 may alternately occur, and thus an interval between steps may be more finely sub-divided. As an interval between steps is finely sub-divided, an operation of transmitting a driving force to the ultrasonic transducer 24 may also be sub-divided. Accordingly, since an operation of controlling rotation of the ultrasonic transducer 24 is more finely sub-divided, an overall system may be precisely controlled.

Figure 5:
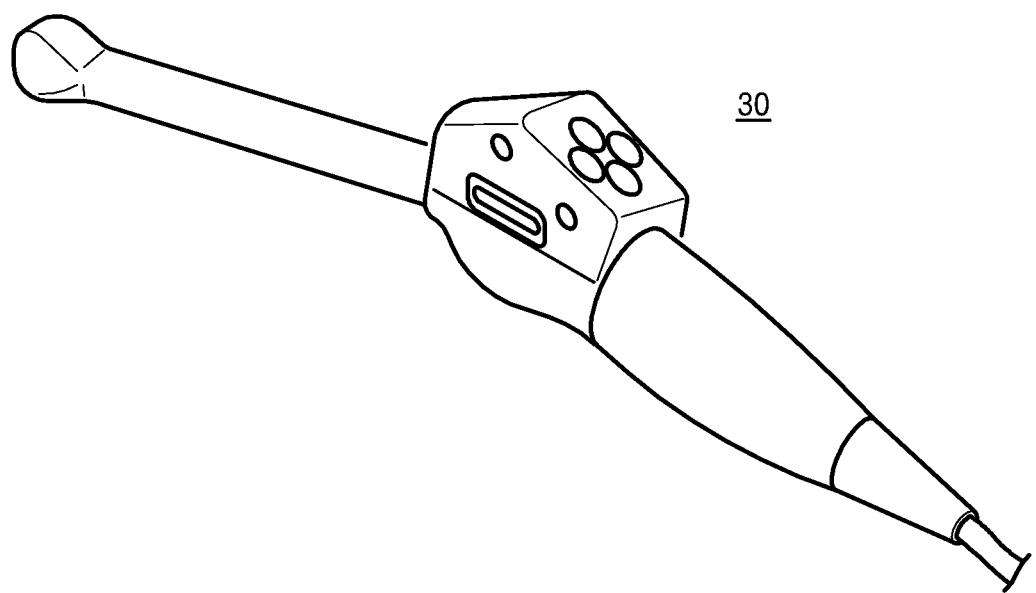
FIG. 5 is a perspective view illustrating an endocavity 3D ultrasonic probe according to an embodiment of the present invention.

In the 3D ultrasonic probe 10 including the ultrasonic transducer 24 in which the ultrasound transmitting/receiving elements 100 are aligned, a region of the object 2 to be diagnosed is determined according to a rotation angle by which the ultrasonic transducer 24 may pivot. In particular, in an endocavity probe 30 of FIG. 5, since a diagnosis is made in a state where the endocavity probe 30 is inserted into a female patient's vagina or anus, a rotation range of the ultrasonic transducer 24 is an essential factor in determining a diagnosis range of the object 2. A conventional ultrasonic probe using a method of transmitting a rotational force by using a gear, a pulley, and a wire to a driving unit has a maximum rotation angle of 120° due to a structure of the wire and thus may not have a sufficient diagnosis range.

Figure 6A:
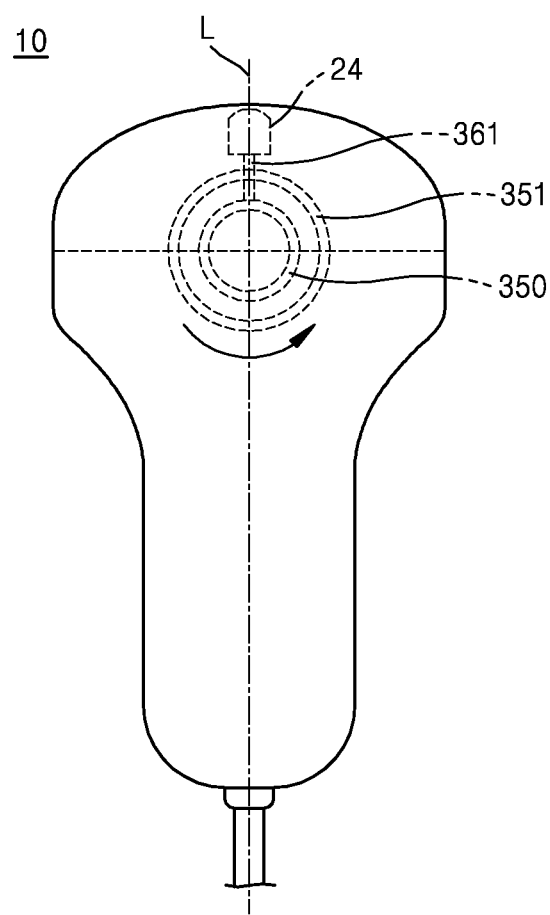
FIG. 6A is a perspective view illustrating a 3D ultrasonic probe according to another embodiment of the present invention.
Figure 6B:
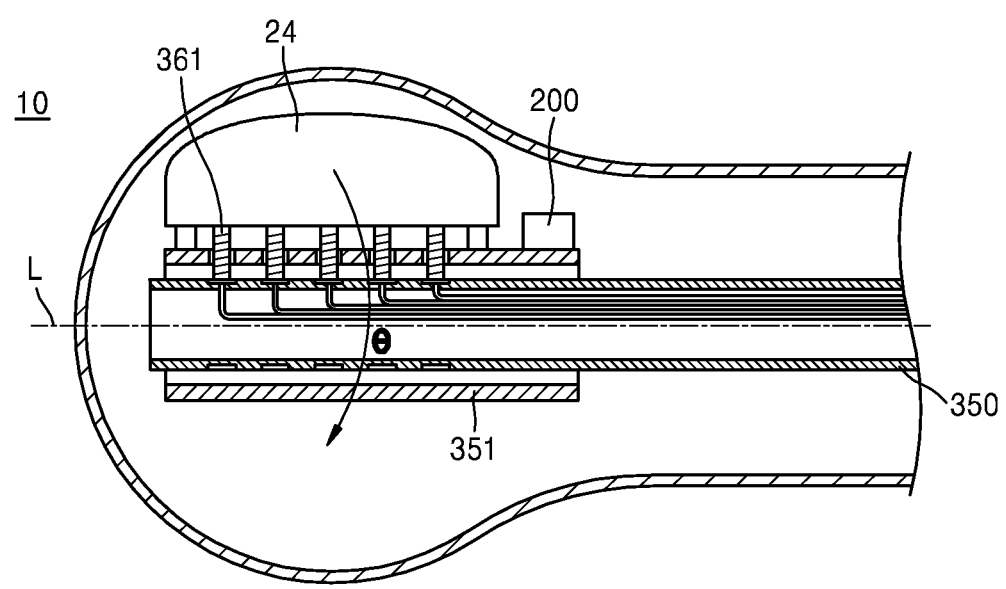
FIG. 6B is a cross-sectional view illustrating the 3D ultrasonic probe of FIG. 6A.

In contrast, referring to FIG. 3, since the rotation axes 340 and 341 of the first and second driving units 200a and 200b are fixed to the both end portions of the ultrasonic transducer 24, a rotation angle of the ultrasonic transducer 24 is not limited by a connection structure that is used to transmit a rotational force that is generated by the first and second driving units 200a and 200b. FIGS. 6A and 6B are views illustrating the 3D ultrasonic probe 10, according to another embodiment of the present invention. Referring to FIGS. 6A and 6B, a rotation axis 350 of a driving unit 200 is formed in a longitudinal direction of the ultrasonic probe 10, and the ultrasonic transducer 24 that is fixed to a bearing 353 that supports the rotation axis 350 rotates about the rotation axis 350 due to a slide unit 361 that is disposed on the bearing 353. In FIGS. 6A and 6B, since the driving unit 200 is disposed to directly drive the rotation axis 350, and thus the ultrasonic transducer 24 may rotate by up to 360° without a limitation of a rotation angle θ due to a power transmission device of the driving unit 200, the 3D ultrasonic probe 10 may diagnose all regions in the object 2 after being inserted.

While one or more embodiments of the present invention have been described with reference to the figures, it will be understood by those of ordinary skill in the art that various changes in form and details may be made therein without departing from the spirit and scope of the present invention as defined by the following claims. Accordingly, the true technical scope of the present invention is defined by the technical spirit of the appended claims.

The use of the terms "a" and "an" and "the" and similar referents in the context of describing the invention (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Finally, the steps of all methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. Numerous modifications and adaptations will be readily apparent to those of ordinary skill in this art without departing from the spirit and scope of the present invention.

What is claimed is:

1. A three-dimensional (3D) ultrasonic probe comprising:
an ultrasonic transducer in which ultrasound transmitting/receiving elements are arranged;
a first driving motor that is disposed at one end of the ultrasonic transducer such that a rotation axis of the first driving motor is coincident with a rotation axis of the ultrasonic transducer, and directly transmits rotational force to the ultrasonic transducer; and
a second driving motor that is disposed at another end of the ultrasonic transducer such that a rotation axis of the second driving motor is coincident with the rotation axis of the ultrasonic transducer, and directly transmits rotational force to the ultrasonic transducer,
wherein the first driving motor comprises a rotor that is disposed at a central portion of the first driving motor and a plurality of stators that surround the central portion of the first driving motor, and the second driving motor comprises a rotor that is disposed at a central portion of the second driving motor and a plurality of stators that surround the central portion of the second driving motor, and
wherein the first driving motor and the second driving motor are respectively disposed at either end of the ultrasonic transducer, and the stators of the first driving motor and the second driving motor which are disposed at either end face each other and are asymmetric to each other.

2. The 3D ultrasonic probe of claim 1, wherein the ultrasound transmitting/receiving elements are aligned on a top surface of the ultrasonic transducer.

3. The 3D ultrasonic probe of claim 1, wherein the first driving motor and the second driving motor are a servo motor or a step motor.

4. The 3D ultrasonic probe of claim 1, wherein a rotation angle of the ultrasonic transducer is equal to or greater than 120° and equal to or less than 360°.

5. The 3D ultrasonic probe of claim 1, wherein the 3D ultrasonic probe is an endocavity probe or a convex probe.

* * * * *